US00PP15419P3

(12) United States Plant Patent
Hammond

(10) Patent No.: US PP15,419 P3
(45) Date of Patent: Dec. 14, 2004

(54) ***CHRYSANTHEMUM* PLANT NAMED 'ESPERANTO HAPPY'**

(50) Latin Name: *Chrysanthemum morifolium*
Varietal Denomination: Esperanto Happy

(75) Inventor: Richard Hammond, Gran Canaria (ES)

(73) Assignee: Aurora Varieties S.L. (ES)

( * ) Notice: Subject to any disclaimer, the term of this patent is extended or adjusted under 35 U.S.C. 154(b) by 0 days.

(21) Appl. No.: 10/670,429

(22) Filed: Sep. 23, 2003

(65) Prior Publication Data

US 2004/0060089 P1 Mar. 25, 2004

Related U.S. Application Data

(60) Provisional application No. 60/413,586, filed on Sep. 24, 2002.

(51) Int. Cl.[7] ..... A01H 5/00
(52) U.S. Cl. ..... Plt./286
(58) Field of Search ..... Plt./286

(56) References Cited

U.S. PATENT DOCUMENTS

PP11,758 P2 1/2001 VandenBerg ..... Plt./286
2003/0121087 P1 6/2003 Hammond ..... Plt./286

OTHER PUBLICATIONS

2000 Ficor Catalog, published Nov. 9, 1999, listing *Chrysanthemum* variety 'Esperanto' under the commercial name 'Esperanza.' See pp. 4 and 13.

2001 Ficor Catalog, published Oct. 12, 2000, listing *Chrysanthemum* variety 'Esperanto.' See pp. 2 (color photograph), 4 and 9.

2002 Ficor Catalog, published Sep. 25, 2001; listing *Chrysanthemum* varieties 'Esperanto' and 'Esperanto Improved.' See pp. 4, 9, 16 (color photograph) and unnumbered insert.

2003 Ficor Catalog, published Sep. 12, 2002, listing *Chrysanthemum* variety 'Esperanto Improved.' See pp. 2 and 7.

*Primary Examiner*—Anne Marie Grunberg
(74) *Attorney, Agent, or Firm*—Howrey Simon Arnold & White, LLP

(57) ABSTRACT

A new variety of *Chrysanthemum* plant named 'Esperanto Happy', having a good uniform canopy of bright red/yellow striped single flowers with a yellow/green disc. The variety has medium vigor, a free branching and uniform spreading habit, and good foliage presentation.

1 Drawing Sheet

This application claims the benefit of U.S. Provisional Application No. 60/413,586, filed Sep. 24, 2002.

Latin name of the genus and species Botanical classification: *Chrysanthemum morifolium.*

Variety denomination: The new *Chrysanthemum* variety denomination is 'Esperanto Happy'.

BACKGROUND OF THE INVENTION

The present invention comprises a new and distinct cultivar of *Chrysanthemum* botanically known as *Chrysanthemum morifolium*, and referred to by the cultivar name 'Esperanto Happy'.

'Esperanto Happy' originated from a naturally occurring whole plant mutation grown in a controlled planting of the variety 'Esperanto Improved' application Ser. No. 10/677,474 in Valsequillo, Gran Canaria, Spain. The new variety 'Esperanto Happy' has been asexually reproduced by vegetative cuttings in Chichester, West Sussex, United Kingdom and the distinguishing characteristics are retained through successive generations of asexual reproduction.

BRIEF SUMMARY OF THE INVENTION

'Esperanto Happy' is a pot type of *Chrysanthemum* plant variety having red/yellow striped single flowers.

Comparison with Parent

Plants of the new *Chrysanthemum* variety 'Esperanto Happy' are most similar to the parent cultivar 'Esperanto Improved' in plant habitat and growth rate. In side-by-side comparisons in Chichester, West Sussex, United Kingdom, under commercial practice, plants of the new *Chrysanthemum* variety 'Esperanto Happy' compared to plants of the parent cultivar 'Esperanto Improved' in the following characteristics.

1. The new variety 'Esperanto Happy' produces red/yellow striped single flowers whereas the parent cultivar 'Esperanto Improved' produces pink/white striped single type flowers.
2. Plants of the new variety 'Esperanto Happy' have similar inflorescence to the plants of the parent cultivar 'Esperanto Improved'.

BRIEF DESCRIPTION OF ILLUSTRATIONS

Typical specimens of the plant and flowers for the new *Chrysanthemum* variety 'Esperanto Happy' are shown in the accompanying digital photograph. The colors shown are as true as possible within the usual limits of this kind of illustration which is a whole plant view of the new variety 'Esperanto Happy' grown in a pot. The plant shown in the illustration is 53 days from commencement of short days.

DETAILED BOTANICAL DESCRIPTION

The following description of the new *Chrysanthemum* variety 'Esperanto Happy' is of plants grown in a greenhouse in Chichester, West Sussex, United Kingdom in the month of February. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 5000 to 6000 foot candles. The plants respond well to the use of growth retardant, such as B9 treatment. To produce a commercial product the plants may be pinched once with the center bud removed. The typical container size for commercial growth is 14 cm. It has been observed that the shelf life of the new variety is about 24 days with a response time of about 8 weeks. The new variety is suitable for growth in a temperature range of 17° C. to 28° C.

The following description is with respect to a plant produced as pot *Chrysanthemum*. In the description of this new *Chrysanthemum* variety, color values have been taken from The Royal Horticultural Society Colour Chart (R.H.S.C.C.).

Plant

Plant type: Pot.
Habit: Upright and free branching.
Height: 23 cm.
Width: 35 cm.
Branching characteristics: Upright and free branching.
Length of lateral branches: 6–11 cm.
Number of breaks from pinch: 3–5.
Stem color: 137A.
Response time: 53 days.
Vigor: Medium.
Shelf life: 24 days.
Disease/pest (susceptibility/resistance observed): None observed to date.
Growth retardant type and treatment: 3 applications of 2.5 gm/"liter" B9 at 2, 21, 28 days after the commencement of sticking of unrooted cuttings. The plants were grown for 3 weeks in Long Day conditions (20 hours of light) and then transferred to Short Day conditions (13 hours of dark).
Propagation:
*Type.*—Vegetative propagation via stem cuttings
*Time to rooting.*—12–14 days with soil temperatures of 18° C.
*Rooting habit.*—Fine and fibrous.

Foliage

Number of leaves per lateral branch: 8–11.
Compound or single: Single.
Arrangement of leaves: Alternate.
*Shape of leaf.*—Typically 5 lobed ovate.
*Size of leaf.*—Width (cm): 3.5–7 Length (cm): 5–10.
*Leaf apex.*—Acute.
*Base.*—Obtuse.
*Attachment.*—Petioled.
Aspect: Slightly undulating.
Margin: Palmately lobed.
Surface characteristics:
*Top.*—Slightly pubescent.
*Bottom.*—Pubescent.
Petiole:
*Color.*—137B. Length: 1.5 cm.
Venation: net prominent midvein at underside.
*Color.*—Upper side: Near 137A. Under side: Near 138A.
Color:
*Mature leaf, upper side.*—Near 137A; under side: Near 138A.
*Young leaf, upper side.*—Near 137B; underside: Near 138B.

Flower

Flower appearance: Circular slightly cupped.
Flower type: Single.
Flower form: Cupped.
Flower shape: Circular.
Flowering habit: Cyme.
Number of blossoms per branch: 3–5.
Inflorescence form: Pyramidal.
*Depth of fully expanded blossoms.*—2 cm.
*Diameter of fully expanded blossoms.*—6–8 cm.
Phyllaries:
*Number.*—28–30.
*Color.*—Near 136C.
*Length.*—0.5–0.9 cm.
*Width.*—0.2–0.4 cm.
*Texture/appearance.*—Pubescent.
Peduncle: Peduncle length is shortest at the terminal flower and progressively longer moving down the stem.
*Length.*—2.5–10 cm.
*Color.*—Near 136C.
*Surface.*—Pubescent.
*Habit.*—Slightly curving.
*Strength.*—Medium.
Pedicel: Length: terminal: 1.5–3.5 cm; lateral: 1.5–6 cm.
*Color.*—Near 138B.
*Surface.*—Pubescent.
*Habit.*—Slightly curving.
*Strength.*—Medium.
Ray florets:
*Form/shape.*—Straight.
*Texture/appearance.*—Matte.
*Number per flower.*—25–30.
*Length.*—3–3.5 cm; Width: 0.8–1.2 cm.
*Apex.*—Rounded.
*Base.*—Tapered.
*Margin.*—Entire.
Disc florets:
*Form/shape.*—Cylindrical.
*Texture/appearance.*—Shiny.
*Number per flower.*—170–250.
*Length.*—0.3–0.6 cm; Width: <0.1–0.1 cm.
*Diameter of disc.*—1.2–1.5 cm.

Fragrance: Faint.

Flower bud (at onset of color):

*Length.*—1.5 cm.

*Diameter.*—1 cm.

*Form/shape.*—Globular.

*General flower color.*—1. Ray florets, upper side: Immature: Near 46B and 9A. Mature: Near 46C and 9B. Older/Fading: Near 46D and 9C. 2. Ray florets, under side: Immature: Near 4A. Mature: Near 4B. Older/Fading: Near 4C. 3. Disc florets: Immature: Near 144A. Mature: Near 154A. Older/Fading: Near 154B. 4. Bud 138B.

Flower progression with age: Flower form does not change with age but there is a slight colour fading.

Other distinguishing characteristics: Foliage remains good with age.

Reproductive Organs

Lastingness of blooms: About 24 days.

Gynoecium present on Ray and Disc florets;

*Ray florets per individual flower.*—Pistil Number: 25. Stigma color: Near 6C. Stigma shape: Forked. Style Color: Near 6C. Style Length: 0.2 cm.

*Disc florets per individual flower.*—Pistil Number: >30<45. Stigma color: Near 6C. Stigma shape: Forked. Style Color: Near 6C. Style Length: 0.2 cm.

Androecium: None observed to date.

Fruit and Seeds: None observed to date.

What is claimed is:

1. A new and distinct variety of *Chrysanthemum* plant, substantially as described and illustrated herein.

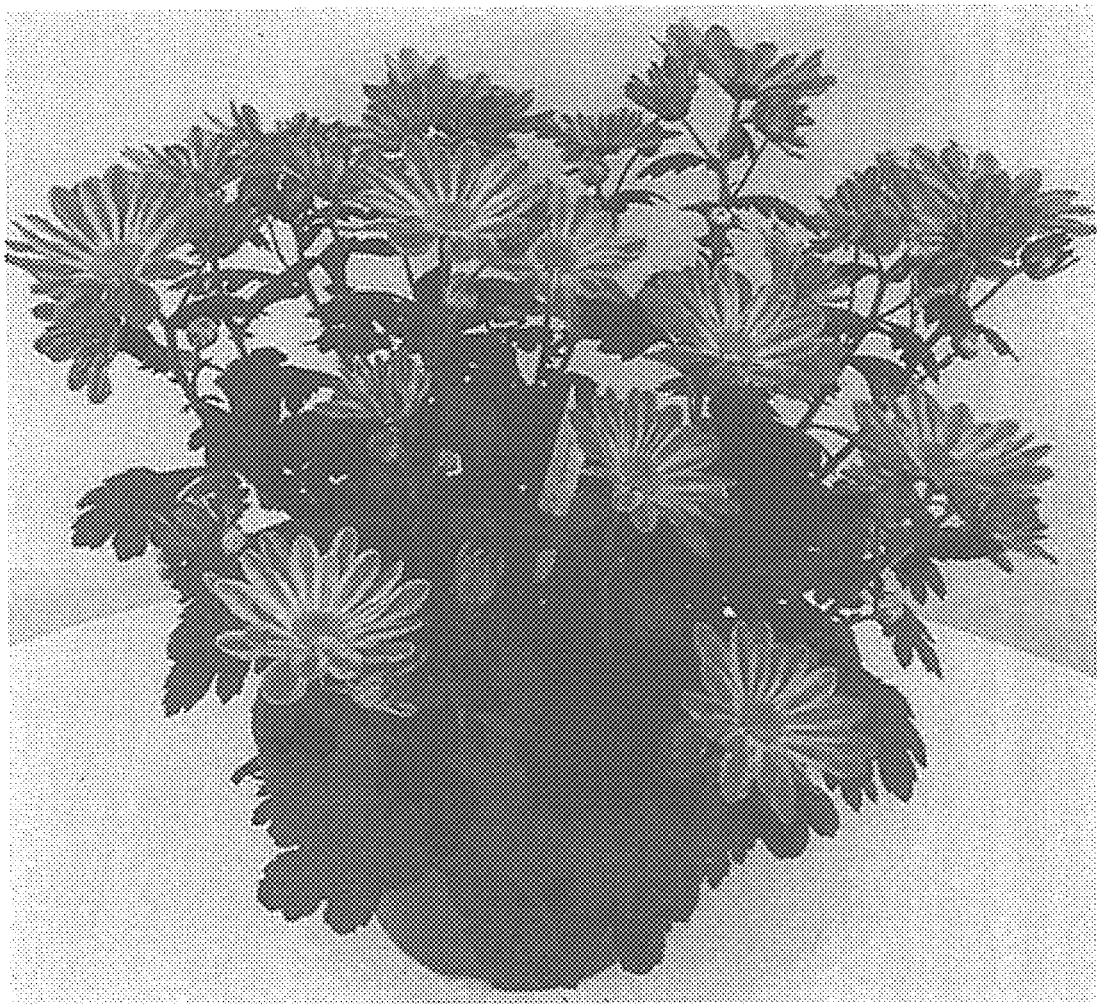

* * * * *